United States Patent [19]

Reitz et al.

[11] 4,247,671
[45] Jan. 27, 1981

[54] HYDROCURABLE COMPOSITIONS CONTAINING OXAZOLINE GROUPS

[75] Inventors: R. Larry Reitz, Salem, Conn.; Thomas W. Hutton, Doylestown; Sheldon N. Lewis, Willow Grove, both of Pa.

[73] Assignee: Rohm and Haas Company, Philadelphia, Pa.

[21] Appl. No.: 29,225

[22] Filed: Apr. 11, 1979

Related U.S. Application Data

[62] Division of Ser. No. 809,742, Jun. 24, 1977.

[51] Int. Cl.³ ............................................. C08F 26/06
[52] U.S. Cl. .................................... 526/260; 548/237
[58] Field of Search ...................... 526/260; 260/307 F

[56] References Cited

U.S. PATENT DOCUMENTS

| | | | |
|---|---|---|---|
| 3,483,145 | 12/1969 | Levy | 260/307 F |
| 3,609,161 | 9/1971 | Dowbenko | 260/307 F |
| 3,711,433 | 1/1973 | Willey | 526/260 |
| 3,737,408 | 6/1973 | Hunsucker | 260/307 F |
| 3,753,935 | 8/1973 | Miller | 260/22 CA |
| 4,103,093 | 7/1978 | Lewis | 526/310 |

FOREIGN PATENT DOCUMENTS

959999 12/1974 Canada .

*Primary Examiner*—Paul R. Michl
*Attorney, Agent, or Firm*—Lester E. Johnson

[57] ABSTRACT

Novel oxazoline-containing monomers represented by the formula

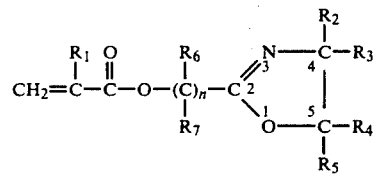

wherein:
n is an integer of from 1 through 20:
$R_1$ is selected from the group consisting of hydrogen and methyl; and
$R_2$, $R_3$, $R_4$, $R_5$, $R_6$ and $R_7$ are independently selected from the group consisting of hydrogen and alkyl of from 1 through 20 carbon atoms;

polymers thereof, and methods for preparing the same are disclosed.

The hydrocurable polymers of the invention, before hydrolysis, contain a plurality of units represented by the following formula:

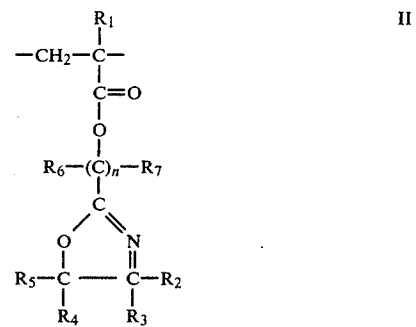

Polymers having such units may be obtained by addition polymerization of monomers of structure I, preferably with other ethylenically unsaturated monomers. In the alternative, polymers may be obtained by transesterification of polymers having pendant ester groups, (for example those having 1 through 5 carbon atoms in the alcohol moiety, such as polymers containing methyl mthacrylate, butyl acrylate, and the like), by an alcohol represented by the formula

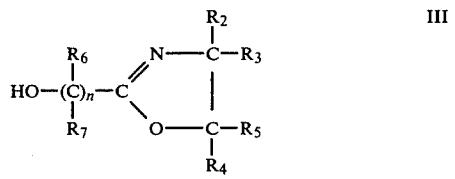

wherein $R_2$—$R_6$ are as noted above.

A third method of obtaining units represented by structure II is by direct esterification of —COOH (carboxyl) units in a polymer, by an alcohol of formula III. This latter route, while possible, generally is not preferred. The oxazoline-containing polymers are blended with addition polymers containing a plurality of dicarboxylic acid cyclic anhydride groups, and the blended materials are caused to react with each other in the presence of moisture whereby they become crosslinked into a ripple-free, smooth coating by a novel two-step process. The process steps involve a first heat treatment to melt the blended materials followed, while the compound is still hot, by a moisture treatment to crosslink and set the resin mixture. Alternatively, the cure may be conducted slowly enough to permit fusion in the presence of moisture, followed by crosslinking. The blended materials may be applied to a suitable substrate from a solution, from a nonaqueous dispersion, or, preferably, as a powder.

14 Claims, No Drawings

HYDROCURABLE COMPOSITIONS CONTAINING OXAZOLINE GROUPS

This is a division of application Ser. No. 809,742 filed June 24, 1977.

BACKGROUND OF THE INVENTION

A. Field of the Invention

This invention relates to poly(oxazoline) compounds and more particularly to a method of making hydrocured thermoset polymers derivable from 2-(4,4-dimethyl-2-oxazolinyl)-5-pentyl substituted esters and the like, the oxazoline-containing monomers themselves and their use in coatings, particularly where applied as a powder coating. The hydrocured thermoset polymers are obtained by blending a polymer containing a plurality of units of oxazoline-containing esters of acrylic and methacrylic acids with a polymer containing a plurality of units derived from addition polymerizable ethylenically unsaturated dicarboxylic acid cyclic anhydrides, followed by heating the combined materials to fuse the blend and achieve uniform flow of the fused blend on the substrate to be coated. Crosslinking to set the fused blend is achieved by exposing the heated materials to moisture.

B. Prior Art

Durable inexpensive thermosetting polymers, particularly those useful as coating materials, are in continual demand for a myriad of applications. In today's large scale industrial applications of polymer coating materials, the need for eliminating solvents with their inherent hazard and disposal problems becomes an important focus point in the development of new thermosetting polymer materials. Of these thermosetting polymers, those which are suitable for use in powdered form are of particular interest today in light of their ability to be applied by electrostatic processes. However, the powdered polymers have problems associated with their use. Chief among these problems is the poor quality of the finished film which is often marked by a rippled appearance known in the trade as "orange peel". Orange peel results from the competition of polymer cure with polymer "flow-out", a condition generally heretofore believed inherent in the nature of thermosetting resins.

Some polymerizable oxazolines are known and, in the prior art, a few of the known oxazolines have found application as coating materials.

U.S. Pat. No. 3,609,161 to Dowbenko discloses polymerizable 2,4-dialkyl-2-oxazoline-4 alkyl acrylates. U.S. Pat. No. 2,410,318 to Tryon discloses the reaction of acid anhydrides with 2-oxazoline. Polymethylene bis-2-oxazolines and their reactions with maleic anhydride polymers are shown in U.S. Pat. Nos. 2,543,602 and 3,547,498 to Rowland. British Pat. No. 1,198,708 (1970), related to U.S. Pat. Nos. 3,493,568 and 3,542,699, discloses the synthesis of 2-(5-hydroxypentyl)-2-oxazoline from caprolactone and ethanolamine. Meyers in *Tetrahedron Letters*, 1972, at p. 3031 discloses the preparation of 2-(5-hydroxypentyl)-4,4-dimethyl-2-oxazoline. U.S. Pat. No. 3,753,935 shows copolymers of vinyl oxazolines and other unsaturated monomers.

However, the prior art references fail to disclose a suitable oxazoline ester capable of producing a smooth, ripple-free surface when applied as a thermosetting powder resin. Likewise there has not been available a thermosetting resin which, when applied as a powder coating, is capable of satisfactorily selectively separating the melting and flowing step from the curing step or steps.

SUMMARY OF THE INVENTION

The aforesaid prior art problems are overcome by the compositions of this invention and the process for applying these compositions as a coating.

In one aspect, this invention comprises novel 2-hydroxyalkyl-2-oxazoline monomers represented by the formula

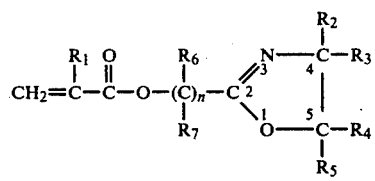

wherein, in this and other formulae herein unless other noted, n is an integer of 1 through 20;

$R_1$ is selected from the group consisting of hydrogen and methyl;

$R_2$, $R_3$, $R_4$, $R_5$, $R_6$ and $R_7$ are independently selected from the group consisting of hydrogen and alkyl of from 1 through 20 carbon atoms.

Preferably, $R_1$ is methyl.

Preferably, when $R_2$, $R_3$, $R_4$, $R_5$, $R_6$ or $R_7$ is alkyl, the alkyl group contains from 1 to 5 carbon atoms. More preferably, at least one of $R_2$ and $R_3$ is alkyl having up to 5 carbon atoms and $R_4$, $R_5$, $R_6$ and $R_7$ are hydrogen. Most preferably, $R_2$ and $R_3$ are both, independently, alkyl having up to 5 carbon atoms.

In another aspect, this invention comprises a method of preparing the oxazoline-containing monomer of claim 1 represented by the formula

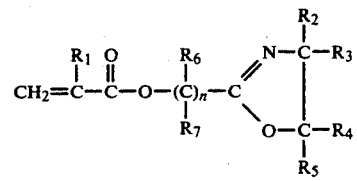

comprising the esterification of an acid represented by the formula

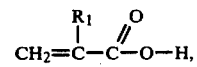

or the transesterification of a $C_1$ to $C_5$ alkyl ester of said acid, with an oxazoline-containing alcohol represented by the formula

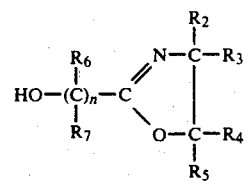

wherein:

n is an integer of from 1 through 20;

$R_1$ is selected from the group consisting of hydrogen and methyl; and $R_2$, $R_3$, $R_4$, $R_5$, $R_6$ and $R_7$ are independently selected from the group consisting of hydrogen and alkyl of from 1 through 20 carbon atoms.

In yet another aspect, this invention comprises an addition polymer having at least five mers and a molecular weight of up to about 2,000,000 and containing in the backbone of said polymer a plurality of units derived from the group consisting of corresponding acrylic, and methacrylic, acid esters represented by the formula

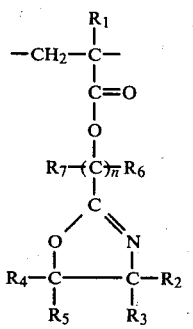

II wherein:

n is an integer of from 1 through 20;

$R_1$ is selected from the group consisting of hydrogen and methyl; and $R_2$, $R_3$, $R_4$, $R_5$, $R_6$ and $R_7$ are independently selected from the group consisting of hydrogen and alkyl of from 1 through 20 carbon atoms.

In still another aspect, this invention comprises a hydrocurable polymer blend, capable of yielding a thermoset polymer, comprising:

(1) a first addition polymer having at least five mers and a molecular weight of up to about 2,000,000 and containing in the backbone thereof a plurality of units derived from the group consisting of corresponding acrylic, and methacrylic, acid esters represented by the formula

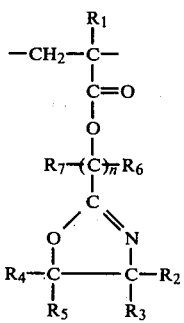

II wherein:

n is an integer of from 1 through 20;

$R_1$ is selected from the group consisting of hydrogen and methyl; and $R_2$, $R_3$, $R_4$, $R_5$, $R_6$ and $R_7$ are independently selected from the group consisting of hydrogen and alkyl of from 1 through 20 carbon atoms; with (2) a second addition polymer containing in the backbone thereof a plurality of units derived from addition polymerizable ethylenically unsaturated dicarboxylic acid cyclic anhydrides; the ratio of said first polymer units to said second polymer units being from about 5:1 to 1:5.

In yet another aspect, this invention comprises a hydrocured thermoset polymer comprising the reaction product, of:

(1) a first addition polymer having greater than five mers and a molecular weight of up to about 2,000,000 and containing in the backbone thereof a plurality of units derived from the group consisting of corresponding acrylic, and methacrylic, acid esters represented by the formula

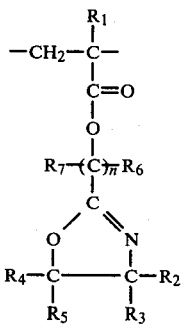

II wherein:

n is an integer of from 1 through 20;

$R_1$ is selected from the group consisting of hydrogen and methyl; and $R_2$, $R_3$, $R_4$, $R_5$, $R_6$ and $R_7$ are independently selected from the group consisting of hydrogen and alkyl of from 1 through 20 carbon atoms; with (2) a second addition polymer containing in the backbone thereof a plurality of units derived from addition polymerizable ethylenically unsaturated dicarboxylic acid cyclic anhydrides; and (3) water; the ratio of said first polymer units to said second polymer units being from about 5:1 to 1:5.

In still another aspect, this invention comprises an article of manufacture comprising the hydrocured thermoset polymer of this invention.

Polymers having units represented by the abovedescribed formula II are obtained by addition polymerizing a monomer mixture comprising oxazoline-containing monomers represented by formula I. Preferably, this polymer is polymerized from a monomer mixture which further comprises from 0 to about 80% by weight of units of other ethylenically unsaturated monomers. The polymers from such monomers have at least five (5) mers and a molecular weight of up to about 2,000,000. Alternatively, the polymers having units represented by above-described formula II are obtained by transesterification of corresponding precursor acrylic polymers having units derived from acrylic, and methacrylic, acid esters wherein the pendant ester groups have from 1 through 5 carbon atoms in the alcohol moiety. Suitable precursor acrylic polymers are polymerized from monomer mixtures comprising, for example, methyl methacrylate, butyl acrylate and the like.

A third method of obtaining polymers having units of structure II is by esterification of —COOH groups in a polymer by an alcohol of the formula

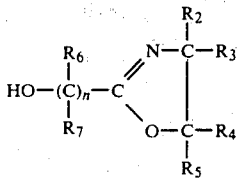

This latter route, while possible, is not preferred.

The oxazoline polymers are blended with addition polymers or compounds containing cyclic anhydride groups, and the blend cured by a two-step process of heat followed by moisture. The molar ratio of anhydride groups to oxazoline groups in the mixture suitably is from 5:1 to 1:5, preferably from 3:2 to 3:5.

The hydrocurable, thermosettable polymer blend of this invention may be utilized as a coating by standard solvent or nonaqueous dispersion application to the article to be coated. It is especially preferable to prepare the hydrocurable, thermosettable polymer blend as a powder and to apply the powdered blend electrostatically or by other powder spreading means to the article to be coated. The crosslinking of the novel polymers of this invention subsequent to fusion, is unique and critical to achieve a ripple-free appearance. It has been discovered that the prior art problem of premature cure may be eliminated by utilizing the polymers of this invention in a selective process which preliminarily heats the resin to achieve proper melt and flow, and then separately crosslinks the resin. This selectivity is achieved by the discovery that the resins of this invention may be prevented from crosslinking and curing if maintained under anhydrous conditions. The coating formulations of this invention remain fluid as long as the reaction zone remains anhydrous even at the high temperatures needed to cause flow, and which heretofore were sufficiently high to cause crosslinking of prior art resins. Since the hydrolysis and crosslinking are not instantaneous, it is possible to obtain good flow and leveling prior to crosslinking simply by introducing the surface containing a film of the hydrocurable, thermosettable polymer blend of the invention directly into a high humidity oven.

The rate of cure depends in part upon whether $R_2$ and $R_3$, in formula II, are both H, one is H and the other alkyl, or both are alkyl. For example, when a polymethylene-2,2'-bis-5-methyl-2-oxazoline (both $R_2$ and $R_3$ are H and there is one methyl group on the 5 position) is blended with a copolymer containing 15% copolymerized maleic anhydride, the mixture containing equal amounts of anhydride and oxazoline functionality, a solvent solution thereof gels in weeks, and a film a mil or so thick cures under ambient conditions in a matter of days. On the other hand, a polymethylene 2,2'-bis-4,4-dimethyl-2-oxazoline (two methyl groups in the 4 position), subjected to the same conditions, does not gel in solution, nor does it cure upon being dried at room temperature for several days. Accordingly, the reason that the 4,4-dialkyl derivative is much preferred is that the blend of the oxazoline ester or resin with the anhydride-containing resin has long term stability.

Thus in the preferred practice of this invention the anhydride-oxazoline polymer mixture, preferably as a powder, is applied to the substrate to be coated, and heated at elevated temperatures of from about 100° C. to about 250° C. preferably from 125° C. to 175° C., in a first zone to achieve proper melt and film flow. After melt and flow is achieved, a second treatment zone containing moisture, for example steam, is provided to achieve crosslinking, similar temperatures being used. A ripple-free coating results.

The hydrocuring reaction can be carried out with or without a catalyst. For instance, p-toluenesulfonic acid is a suitable catalyst, a dibutyltin octoate, zinc chloride, hydrogen chloride, or the like, may be advantageously employed. The acid catalyst will generally be present in an amount of from about 0.001% to about 10% by weight based on the weight of reactants, and preferably from about 0.1% to about 1.0% by weight.

The oxazoline-containing monomers, represented by formula I hereinabove described, of this invention are preferably prepared by the transesterification of monomeric acrylic acid esters, such as, for example, methyl methacrylate, with an appropriate alcohol such as 2-(3-hydroxypropyl)-4,4-dimethyl-2-oxazoline. Preferably, th alcohol moieties of said acrylic acid esters have from 1 to 5 carbon atoms The transesterification reaction can, if desired, be catalyzed. As is well known in the art, suitable catalysts include sodium salts of phenols, such as sodium phenoxide, p-hydroxyphenylamine, or a tetraalkyl titanate, such as tetraisopropyl or tetrabutyl titanate. If the reaction is carried out using a tetraalkyl titanate as the catalyst, about one-half percent to about ten percent, preferably one to five percent, by weight of the titanate based on the weight of the oxazoline is used. No solvent is needed. The starting materials can be used in stoichiometrically equivalent amounts, or the ester compound or oxazoline alcohol can be used in excess of theory. The lower ($C_1$ to $C_5$) alcohol liberated during the transesterification can be removed by fractional or azeotropic distillation. The reaction is generally carried out at temperature of about 50° C. to about 180° C. and completion of the reaction can be determined by measuring the amount of alcohol removed. The theoretical amount of alcohol that should be liberated from the system by distillation is readily calculated.

Basic metal hydroxides can also be used as the transesterification catalysts. They can be used in an amount of from about 0.2% to about 5% and preferably from about 1 to about 3% by weight based on the weight of the starting oxazolidine. Sodium methoxide or sodium ethoxide as well as the potassium and lithium analogs can be used as can magnesium dimethoxide. An illustrative transesterification reaction involves mixing a starting oxazoline alcohol and the compound containing lower alkyl ester groups with a solution of the alkoxide in an alcohol such as methanol. The alkoxide solution can be added gradually to the esteroxazoline mixture. No additional solvent is needed. The temperature may be from 50° C. to about 180° C. and preferably not over 160° C.

The oxazoline alcohol base is itself derived from the condensation of, for example, ε-caprolactone with the appropriate amine, for example 2-amino-2-methyl-1-propanol.

In addition to ε-caprolactone

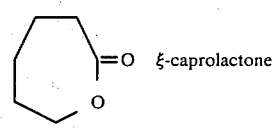

other lactones include the following

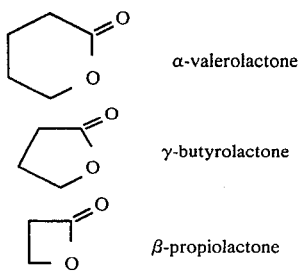 α-valerolactone

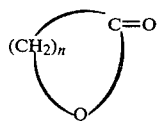 γ-butyrolactone

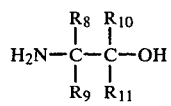 β-propiolactone

These may be represented by the formula $$\underset{(CH_2)_n}{\diagdown}\!\!\!\diagup\!\!\!\overset{C=O}{\underset{O}{\diagup}} \qquad IV$$

wherein n is from 2 to 5 inclusive. Of course, substituted lactones are useful.

The amines useful in making the oxazoline alcohol may be represented by the formula $$H_2N-\underset{R_9}{\overset{R_8}{C}}-\underset{R_{11}}{\overset{R_{10}}{C}}-OH \qquad V$$

wherein, $R_8$, $R_9$, $R_{10}$, $R_{11}$=H or lower alkyl of 1 through 5 carbon atoms, with both $R_8$ and $R_9$ preferably being lower alkyl. Examples of useful aminoethanols are 2-amino-2-methyl propanol, 2-amino propanol, ethanolamine, and the like.

There are two preferred synthesis routes for making the oxazoline-containing polymers-addition copolymerization and transesterification.

Referring first to the addition copolymerization route, there are two methods of making addition copolymers—free radical and anionic. Both the free radical and anionic route utilize monomers of formula I with other ethylenically unsaturated monomers. Examples of ethylenically unsaturated monomers are the esters of α,β-ethylenically unsaturated monocarboxylic acids, α,β-ethylenically unsaturated monocarboxylic acids, α,β-ethylenically unsaturated aldehydes, esters of α,β-ethylenically unsaturated dicarboxylic acids, α,β-ethylenically unsaturated dicarboxylic acids, α,β-ethylenically unsaturated nitriles, hydrocarbons such as α-olefins, conjugated diolefins, vinylaryl compounds, vinyl alkyl ethers, vinyl halides, vinylidene halides, vinyl sulfides, vinyl acyloxy compounds (esters of saturated carboxylic acids and ethylenically unsaturated alcohols), and vinyl ureido monomers.

Specific examples of suitable monomers which may be copolymerized for use according to the invention are esters and half esters of acrylic acid, methacrylic acid, itaconic acid, maleic acid, 4-pentenoic acid, and the like with alkanols having 1 to 20 carbon atoms, such as methanol, ethanol, propanol, butanol, hexanol, dodecanol, pentadecanol, and the like, acrolein, methacrolein, ethylene, propylene, isobutene, butadiene, isoprene, chloroprene, styrene, vinyltoluene, vinyl methyl ether, vinyl isobutyl ether, vinyl chloride, vinyl bromide, vinylidene chloride, vinyl sulfide, vinyl acetate, vinyl propionate, ureido monomers such as are disclosed in U.S. Pat. Nos. 2,881,155 to Hankins, 3,300,429 to Glavis and Keighly, and 3,356,627 to Scott, including β-ureidoethyl acrylate, β-(N,N'ethyleneureido)-ethyl acid maleate, β-ureidoethyl vinyl ether, N-vinyl-N,N'-ethyleneurea, N-vinyloxyethyl-N,N'-ethyleneurea, N-methacrylamidomethyl-N,N'-ethyleneurea, and N-dimethylaminoethyl-N'-vinyl-N,N'-ethyleneurea, N-hydroxyethylacrylamide, N-methylol-acrylamide, and N,N-(dimethylaminoethyl)acrylamide, and the like. The preferred comonomers are styrene and the ($C_1$-$C_4$) alkyl esters of acrylic and methacrylic acids. In general, any addition copolymerizable ethylenically unsaturated organic compound (monomer) containing a vinyl group ($CH_2$=CH—), a vinylidene group ($CH_2$=C<), or a vinylidene group (—CH=CH—) is included among the useful monomers.

Referring to free radical synthesis; the oxazoline-containing copolymers used in the coating composition are prepared by well-known polymerization techniques. Preferably, a solvent is used for the polymerization reaction which can also be employed as the solvent for the coating application. The monomer mixture comprising the oxazoline-containing monomers and other monoethylenically unsaturated compounds in the proportions needed to give the composition hereinabove defined are fed over a period of one to ten hours to the refluxing solvent. Any suitable free-radical initiator soluble in the solvent is introduced. The initiatior may be an azo catalyst or peroxide catalyst such as t-butyl peracetate, benzoyl peroxide, t-butyl hydroperoxide or cumene hydroperoxide. Thereafter, the solution of the copolymer may be cooled and the anhydride-containing polymer may be introduced with adjustment of the solvent content to provide the concentration desired.

The polymers may be obtained by anionic polymerization of an alkyl acrylate or an alkyl methacrylate with compounds of formula I using an alkali metal alkoxide, such as potassium methoxide to obtain low molecular weight polymers. With the alkyl methacrylates, a chain-regulating amount of an alcohol such as methanol is utilized. With the acrylates, only a minor amount of alcohol may be present for best results. These polymers have a narrow molecular weight distribution. It should be noted that in regard to anionic copolymerization that methacrylates are preferred over acrylates. The methacrylic ester polymers are described in U.S. Ser. No. 137,057, filed Apr. 23, 1971 (Canadian Pat. No. 959,999), U.S. Ser. No. 371,921, filed June 20, 1973, U.S. Ser. No. 517,334, Ser. Nos. 517,334, 517,335, and 517,337, all filed Oct. 23, 1974. The acrylic acid ester polymers are described in U.S. Ser. No. 241,177, filed Apr. 5, 1972 (which has been published as Belgian Pat. No. 794,403).

The aforesaid prior applications and patents are incorporated herein by reference as describing methods of making polymers and for suitable methods of modifying polymers to obtain "copolymers".

As described herein, polymers containing units of formula II may be also obtained by transesterification of the pendant ester groups in alkyl acrylate or methacrylate polymers, which have been prepared either by a conventional free radical route or by an alkoxide initiated route.

Typical addition polymerizable ethylenically unsaturated dicarboxylic acid cyclic anhydrides useful in preparing the second addition polymer containing cyclic anhydride groups, described hereinabove, are maleic anhydride, itaconic anhydride, glutaconic anhydride and the like. These anhydride-containing addition polymers are obtained by conventional methods, and the anhydride monomers are copolymerized with the same types of ethylenically unsaturated addition polymerizable monomers as are useful in preparing copolymers containing the oxazoline compound. The quantity of said anhydride in the copolymer is from about 2 to 70% on a weight basis, preferably 5 to 20%. Compounds containing two or more cyclic anhydride groups are also useful in minor amounts (that is, less than 50% by weight) in addition to the cyclic anhydride addition polymers. Examples of such cyclic anhydride compounds are 1,2,4,5-benzenetetracarboxylic anhydride and the product of the reaction of maleic anhydride with drying oils such as, for example, linseed oil.

Preferably, the hydrocurable, thermosettable polymer blend of the invention is a powdered composition that does not contain a solvent. However, a suitable inert solvent can be added to dissolve the first oxazoline-containing polymer and the second cyclic anhydride containing polymers, respectively, for formulating the blend. The solvent is then removed to provide a powdered polymer blend. Alternatively, the polymer blend is supplied as a solution or as a nonaqueous dispersion. Included among the solvents which can be used are toluene, xylene, liquid aliphatic hydrocarbons, isopropyl ether, ethyl acetate, 2-ethoxyethyl acetate, methyl ethyl ketone, and the like, as well as mixtures of such solvents.

Pigments, dyes, fillers, antioxidants and anti-ozonants, stabilizers, flow control agents, or other optional ingredients can also be included.

While fluidized bed or electrostatically applied powder coatings are particularly valuable, the compositions of the present invention are adapted to be applied from solution or nonaqueous dispersions in any suitable fashion to the substrate to be coated, such as by brushing, spraying, dipping, roller coating, or by any other suitable method known in the art. Fusion of the coating is not necessary if applied from a solution. For powder coatings, the Tg of the powder mixture is preferably above about 30° C., i.e., solid at ambient temperature.

The compositions of the invention can be used for coating a wide variety of substrates including metals, paper, plastics, glass, textiles, leather, wood, ceramics, brick, stone, and concrete surfaces. Also, the compositions can be used in forming films, fibers, sealants, paints, floor tile coatings, impregnants, and adhesives for both natural and synthetic material, as well as in a wide variety of other applications.

Preparation of these oxazoline-containing monomers, polymers, and blends, and uses thereof, are best illustrated by the following examples. Unless specifically indicated as otherwise, in these examples and throughout this specification parts and percentages are by weight.

DESCRIPTION OF THE PREFERRED EMBODIMENTS

Example 1

The alcohol, 2-(5-hydroxypentyl)-4,4-dimethyl-2-oxazoline, is prepared by a reaction according to the equation

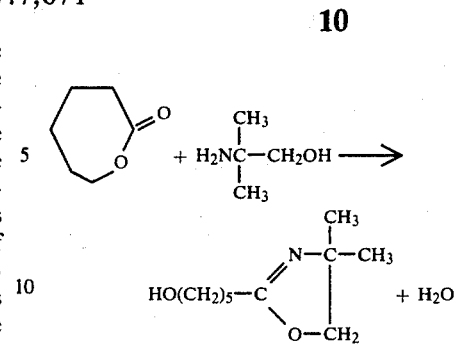

EQUATION I

The reaction represented by Equation I is carried out by the following procedure:

In a round-bottomed flask equipped with a thermometer, stirrer and addition funnel is placed 968 grams of 2-amino-2-methylpropanol. The flask contents are heated to 164° C. and 855 grams of ε-caprolactone are added from an addition funnel over a 30-minute period. The flask is equipped with a 15-plate Oldershaw column. During a nine-hour distillation period, 210 grams of distillate with a boiling point of 100°-161° C. is collected during which time the reaction temperature increases from 171°-220° C. The distillate is titrated with 0.5 N $H_2SO_4$ and found to contain 75.6 g. of 2-amino-2-methylpropanol. The contents of the reaction flask are then distilled at reduced pressure through a six-inch Vigreux column. Distillate, 1099.3 grams with boiling point 140°/7 torr. to 142°/5 torr. is collected as product; NE (neutral equivalent) 185 ($HClO_4$ titration).

Example II

Other alcohols of this series are made in a similar manner by substitution of the appropriate lactone for the ε-caprolactone utilized in Equation I, and the appropriate aminoethanol.

That is, where n=3, the equation becomes

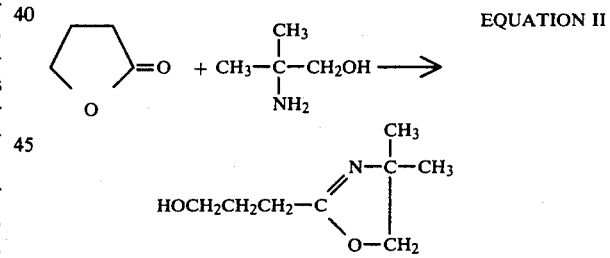

EQUATION II and the alcohol formed is 2-(3-hydroxypropyl)-4,4-dimethyl-2-oxazoline. The following is an example of how to prepare the alcohol of Equation II.

To a round-bottomed flask equipped with a 15-plate Oldershaw column, thermometer and stirrer is added 172 grams of ν-butyrolactone and 267 grams of 2-amino-2-methylpropanol. During an 8-hour period distillate containing the equivalent of 36 grams of water is collected as the reaction temperature increases from 175°-215° C. Distillation through the column at reduced pressure affords 111.6 grams of product with a boiling point 130°-135°/18 torr.; NE (neutral equivalent) 157.7 ($HClO_4$ titration).

Example III

The oxazoline ester 2-(4,4-dimethyl-2-oxazolinyl)-5-pentyl methacrylate is prepared by a reaction according to the equation

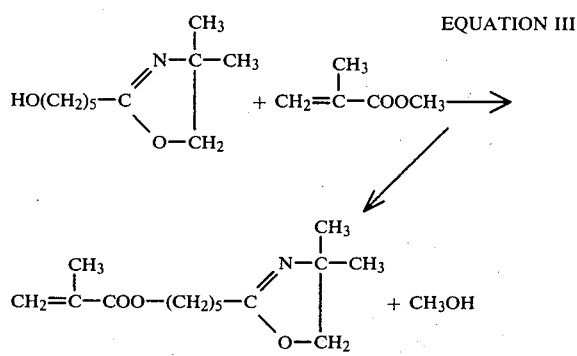

EQUATION III using the following procedure:

To a round-bottomed flask equipped with a stirrer, thermometer, and 15-plate Oldershaw column is added 994 grams of 2-(5-hydroxypentyl)-4,4-dimethyl-2-oxazoline, 2130 grams of methyl methacrylate, 0.3 grams of phenothiazine and 10 milliliters 10% methanolic lithium methoxide. A total of 590 grams of distillate (methyl methacrylate-methanol) is collected with a boiling point of 40°-58° C. at 198 torr. which when analyzed contains 169.8 grams of methanol. The contents of the reaction flask are analyzed by gas-liquid chromotograph and found to contain 18.2% methyl methacrylate and 80% 2-(4,4-dimethyl-2-oxazolinyl)-5-pentyl methacrylate. A pure sample of the methacrylate derivative is obtained by distillation of the solution at reduced pressure. The methacrylate has a boiling point of 125°-126°/1.6 torr.; $N^{25}D$ 1.4597; NE ($HClO_4$ titration), 253.

It is not necessary to isolate the oxazoline ester, since any of the original unreacted ester such as methyl methacrylate will copolymerize.

Other esters appropriate for this invention may be made in similar manner by replacing the methyl methacrylate with the appropriate ester starting material.

It is possible, however, where a polymer is to be a resin component, to transesterify the polymer itself, rather than using the monomeric oxazoline ester.

Example IV

Transesterification of a low molecular weight polymer of butyl acrylate with 2-(3-hydroxypropyl)-4,4-dimethyl-2-oxazoline.

To a flask is charged 15.1 grams of an 84.8% solution in toluene of oligomeric butyl acrylate ($\overline{M}w$ about 1,000, 7-8 mers), 25.6 grams of xylene, 7.89 grams of 2-(3-hydroxypropyl)-4,4-dimethyl-2-oxazoline and 0.69 milliliters of 25% sodium methoxide in methanol. Distillate containing methanol, toluene and xylene is distilled from the reaction mixture through a spining-band column. After four hours the mixture is recatalyzed with 0.23 milliliters of 25% sodium methoxide. After six hours a total of 9.4 grams of distillate shown to contain 3.72 grams of butanol is collected. The solution in the reaction vessel is collected as product and found to contain 1.47 meq. of basic nitrogen/g.

Example V

Another example of a type of copolymerization useful in this invention follows.

Copolymerization of methyl methacrylate and 2-(4,4-dimethyl-2-oxazolinyl)-5-pentyl methacrylate.

To a dry, round-bottomed flask is added 49 grams of benzene, 3.26 grams of methanol and 5.71 grams of potassium tert-butoxide. Flask contents are heated to 60° C. and a charge of 11.1 grams of benzene, 15.7 grams of methyl methacrylate and 31.5 grams of a solution containing 18.2% methyl methacrylate and 80% 2-(4,4-dimethyl-2-oxazolinyl)-5-pentyl methacrylate is added over 25 minutes. One and one-half hours after the addition, a mixture of 111.9 grams of benzene, 150.3 grams of methyl methacrylate and 318.5 grams of a solution containing 18.2% methyl methacrylate and 80% 2-(4,4-dimethyl-2-oxazolinyl)-5-pentyl methacrylate is added over a one-hour period. The reaction mixture is maintained at 60° C. One hour after the addition a gas liquid chromotograph check indicates essentially no methyl methacrylate remaining. The reaction mixture is quenched by the addition of 3.0 grams of acetic acid. Benzene (150 grams) and 15.8 grams of a filter aid are added, and the product passed through a filter and found to have a 95.3% conversion of oxazoline. The final product is a 71% solids solution of a MMA/CAPOXMA copolymer containing 1.54 meq./g. of basic nitrogen with $\overline{M}n$ 1930 and $\overline{M}w$ 3250. (See Table I for abbreviations).

A solution prepared from 12.0 grams of the above 71% solution of the copolymer, 25.2 grams of a 51.7% toluene solution of a methyl methacrylate/butyl acrylate/styrene/maleic anhydride copolymer in the ratio (35/32/18/15) as prepared in Example VII and 16.4 grams of Solvesso 100, is spread as a 10 mil (0.254 mm) film on a steel plate. Then the film is cured for 30 minute in a high humidity oven at 150° C. The cured film 2.2 mil (0.056 mm) has a direct impact of 18 in-lb. (0.21 kg-m).

Example VI

Copolymers utilizing the monomeric oxazolines of this invention are illustrated by the following example. The preparation of a methyl methacrylate/butyl acrylate/2-(4,4-dimethyl-2-oxazolinyl)-5-pentyl methacrylate (65/5/30) copolymer is as follows.

To 480 grams of refluxing toluene in a reaction flask is added over a three-hour period, at a constant rate, a monomer mixture composed of 232.7 grams of methyl methacrylate, 20.0 grams of butyl acrylate, 150 grams of a mixture containing 27.3 grams of methyl methacrylate and 120 grams of 2-(4,4-dimethyl-2-oxazolinyl)-5-pentyl methacrylate, and 11.0 grams t-butyl peroctoate. Fifteen minutes after the monomer addition is complete a solution of 1.4 grams of t-butyl peroctoate and 140 grams of toluene is added over 30 minutes. The reaction mixture is then held at reflux for 15 minutes. The product is found to contain 38.2% solids (theoretical solids 38.6%) and 0.7% unreacted 2-(4,4-dimethyl-2-oxazolinyl)-5-pentyl methacrylate. A portion of the product is concentrated to 50.6% solids; viscosity 278 cps; basic nitrogen content 0.622 meq./g., $\overline{M}n$ 5500; $\overline{M}w$ 19,400.

The 38.2% solids product solution, 50 grams, is mixed with 6.0 grams of Solvesso 100 and 30.2 grams of a methyl methacrylate/butyl acrylate/styrene/maleic anhydride (35/32/18/15) copolymer as prepared in Example VII as a 51.7% solution in toluene. A film (10 mil) of the solution is cast and cured in a high humidity oven at 150° C. for 30 minutes. The cured film has a swelling ratio of 1.8 (methyl ethyl ketone) and a direct impact of 8 in-lb. (0.092 kg-m).

Example VII

This example illustrates the preparation of the anhydride containing addition polymer component of the moisture curable composition of the invention.

Preparation of copolymer methyl methacrylate/butyl acrylate/styrene/maleic anhydride=35/32/18/15.

To a three-liter, four-necked flask equipped with a one-liter addition funnel, thermometer, stirrer and reflux condenser is added 610 grams toluene. The contents are heated to reflux and maintained under a nitrogen blanket while a monomer mix of 112.5 grams maleic anhydride, 262.5 grams methyl methacrylate, 240 grams butyl acrylate, 135 grams styrene and 28.0 grams benzoyl peroxide are fed at a uniform rate over a three-hour period to the refluxing toluene. The contents are held for 15 minutes, a sample is taken, and a chaser catalyst of 140 grams toluene a 3.75 grams benzoyl peroxide is added over 30 minutes. Reflux is maintained for an additional 30 minutes, the flask is then equipped with a Dean-Stark trap and 20.6 grams of toluene-water removed after a 45-minute reflux. The final product has a solids content of 51.7% (104.2% conversion); a viscosity of 890 cps; anhydride 0.698 meq/g. and anhydride plus acid (using tetra-n-butyl ammonium hydroxide) 0.705 meq/g.; $\overline{M}n$ 4,000; $\overline{M}w$ 14,500.

Example VIII

This example illustrates the preparation of a polyoxazoline by transesterification of a low molecular weight polymer.

To a dry reaction flask equipped with stirrer, thermometer, condenser and addition funnel is added xylene (123 g.) and potassium tert-butoxide (19 g.). While maintaining a blanket of nitrogen, butyl acrylate (1090.0 g.) is added over a one-hour period at a reaction temperature of 67°–73° C. After the addition is completed, the contents are helf at 70° C. for three hours and then quenched by the addition of 99% sulfuric acid (9.0 g.). The contents are stirred for 15 minutes and stripped of solvent and unreacted butyl acrylate at 135° C. and 30 mm. Hg. The contents are cooled to afford a light yellow syrup of 97% solids and 500 cps. viscosity. In a dry flask equipped with a stirrer, thermometer and 10-plate Oldershaw column is placed 132 grams of the above polymer solution, 87 grams of 2-(5-hydroxy pentyl)-4,4-dimethyl-2-oxazoline. (See Example I), 332 grams of xylene and 2.34 grams of dibutyl tin oxide. With the distillation head set at 50% take-off 119 grams of distillate is collected over five hours during which time the pot temperature increases from 145° C. to 151° C. and the head temperature from 120° C. to 139° C. The cooled solution is filtered and stripped of solvent at reduced pressure. The resulting fluid polymer is found to contain 2.07 meq. of basic nitrogen/gram of which 5.1% is unreacted hydroxypentyloxazoline, and have $\overline{M}n$ 1470 and $\overline{M}w$ 2700. The calculated copolymer composition is then BA/2-(4,4-dimethyl-2-oxazolinyl)-5-pentyl acrylate=53/47.

The composition, physical properties and performance data on the polymers and precursors of this invention are outlined in Tables I, II and III.

Table I shows data on maleic anhydride copolymers, suitable as reactants with the oxazolines of this invention, and various specific oxazoline-containing polymers and esters used therewith to prepare hydrocurable compositions. The oxazoline compounds and those containing anhydride functions outlined in Table I are prepared following the procedures of Examples I–VIII, described heretofore.

Referring to Table II, the code column contains a reference number or letter which indicates an anhydride or oxazoline component which may be found described fully in Table I. The other columns give the characteristics of the thermosettable mixture and the properties of the thermoset, hydrocurable film.

The films whose properties are listed in Table II are prepared as follows: Nominal 40% solids solutions are prepared in toluene, and 10 mil (0.254 mm) films cast on glass plates. The film is air-dried for thirty minutes at ambient conditions and cured at the indicated temperature and time in a humid oven.

Table III also lists data on films prepared according to this invention. Table III utilizes oxazoline and anhydride functions according to Table I as indicated in the code column. Table III also lists film thicknesses and swelling ratios. In Table III, the film is formed by casting the film from solution onto Bondorite 100. Bonderite100 is a zinc phosphate treated cold-rolled steel.

Table III also contains data on the direct impact testing of the indicated resin film.

TABLE I

| Description of Oxazoline and Anhydride Components | | | |
|---|---|---|---|
| Code | Description | $\overline{M}n$ | $\overline{M}w$ |
| Part 1: | Oxazoline Component | | |
| A | Copolymer: MMA/CAPOXMA = 54/46 | 1,500 | 2,100 |
| B | Copolymer: MMA/EA/CAPOXMA = 35/30/35 | 4,700 | 18,100 |
| C | BA homopolymer partially transesterified with CAPOX; BA/CAPOX = 53/47 | 1,470 | 2,700 |
| D | MMA/EA/CAPOXMA = 34/31/35 | 5,400 | 27,600 |
| E | MMA/CAPOXMA = 65/35 | 8,600 | 41,000 |
| Part 2: | Anhydride Component | | |
| 1 | MMA/BA/S/MAn = 59.6/25/8.4/7 | 5,300 | 21,200 |
| 2 | MMA/BA/S/MAn = 45.8/30/13.2/11 | 5,100 | 22,200 |
| 3 | MMA/BA/S/MAn = 35/32/18/15 | 5,500 | 24,100 |
| 4 | MMA/BA/MAn = 59/30/11 | 4,300 | 17,900 |

Abbreviations

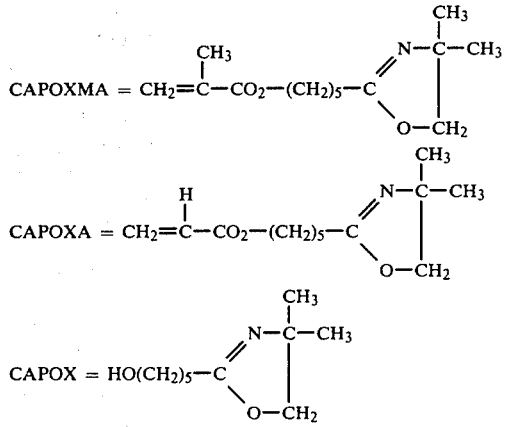

MMA = methyl methacrylate
EA = ethyl acrylate
BA = n-butyl acrylate
S = styrene
MAn = maleic anhydride

TABLE II

FILM PROPERTIES[a] OF ANHYDRIDE/OXAZOLINE COMPOSITIONS

| Code Anhydride Component | Code Oxazoline Component | Equiv. Ratio Anh./Oxa. | Film Thickness (mils) | Film Thickness (mm) | Swelling Ratio | Cold Crack Cycles Passed | 140° F. Print Resistance Rating[d] |
|---|---|---|---|---|---|---|---|
| 1 | A | 1.0/0.85 | 1.8 | 0.046 | 4.6 | 2 | VL |
|   |   | 1/1 | 1.9 | 0.048 | 4.2 | 2 | VL |
|   |   | 1/1.15 | 1.5 | 0.039 | 3.0 | 3 | VL |
| 2 | A | 1.0/0.85 | 2.8 | 0.071 | 1.9 | 10 | VL |
|   |   | 1/1 | 3.1 | 0.079 | 2.4 | 10 | L |
|   |   | 1/1.15 | 2.6 | 0.066 | 2.5 | 10 | VL |
| 3 | A | 1/1 | 3.5 | 0.089 | 1.6 | 10 | VL |
| 4 | A | 1/1 | 3.1 | 0.079 | 3.3 | 2 | L |
| 1 | B | 1/1 | 2.3 | 0.058 | 2.2 | 2 | L |
| 2 | B | 1/1 | 2.8 | 0.071 | 1.8 | 10 | L |
|   |   | 1/1[b] | 2.3 | 0.058 | 2.1 | 10 | L-M |
|   |   | 1/1[c] | 2.5 | 0.064 | 2.1 | 10 | L-M |
| 2 | C | 1/1 | 2.7 | 0.069 | 1.9 | 10 | L-M |

[a] Cured at 150° C., 18 hours, forced draft oven initially containing water
[b] This film cured 1 hour at 150° C. with water vapor.
[c] This film cured 1 hour at 176° C. with water vapor.
[d] VL = very light
L = light
L-M = light-medium

TABLE III

Film Properties of Anhydride/Oxazoline Compositions

| Code Anhydride Component | Code Oxazoline Component | Cure Temp. (30 Min.) | Film Thickness (Mils) | Film Thickness (mm) | Swelling Ratio | Direct Impact in-lb | kg-m |
|---|---|---|---|---|---|---|---|
| 3 | B | 150 | 1.6 | 0.041 | 1.7 | 20–26 | 0.23–0.29 |
|   |   |     | 2.5 | 0.064 | 1.6 | 15–20 | 0.17–0.23 |
| 3 | D | 135 | 2.3 | 0.058 | 2.1 |       |       |
|   |   | 150 | 2.1 | 0.053 | 1.9 | 20–25 | 0.23–0.29 |
|   |   | 175 | 2.1 | 0.053 | 2.1 | 20–25 | 0.23–0.29 |
|   |   | 190 | 1.9 | 0.048 | 2.1 | 20–25 | 0.23–0.29 |
| 2 | D | 135 | 2.4 | 0.061 | 2.0 | n.d. |       |
|   |   | 160 | 2.4 | 0.061 | 2.1 | n.d. |       |
|   |   | 175 | 2.0 | 0.051 | 2.1 | n.d. |       |
| 3 | E | 135 | 1.5 | 0.039 | 2.6 | n.d. |       |
|   |   | 150 | 1.4 | 0.036 | 2.3 | 20   |       |
|   |   | 175 | 3.2 | 0.081 | 1.5 | 20–25 | 0.23–0.29 |
| 2 | E | 135 | 2.1 | 0.053 | 2.3 | n.d. |       |
|   |   | 150 | 2.1 | 0.053 | 2.1 | 10–15 | 0.12–0.17 |
|   |   | 175 | 2.0 | 0.051 | 2.5 | 0–15  | 0.12–0.17 | n.d. = not determined

Example IX

The following illustrates a method for preparing a pigmented powder coating by a solution method utilizing one of the polymers of this invention.

A pigment blend is prepared from titanium dioxide pigment, sand (both of which are previously dried at 105° C.) and a copolymer of methyl methacrylate/butyl acrylate/styrene/maleic anhydride in the ratio of 35/32/18/15 as a 20% solution in toluene. The pigment to resin ratio is 5:1. Then the pigment blend (91.0 grams solids), methyl methacrylate/butyl acrylate/styrene/maleic anhydride copolymer in the ratio of 35/32/18/15 by weight (97.7 grams solids as a 20% solution in benzene) and a copolymer of methyl methacrylate/2-(4,4-dimethyl-2-oxazolinyl)-5-pentyl methacrylate in the ratio of 45/55 by weight (64.3 grams solids as a 20% solution in benzene) are mixed, distributed into four 2-liter flasks and diluted to 10% solids with benzene. The benzene solutions are freeze-dried, the powder ground in a "Waring" blender, and sieved to produce a final product.

The powder which passes through No. 150 mesh, U.S. Sieve Series, is electrostatically sprayed on the Bonderite 100 panels. The panels are baked in an oven at 175° C. for 10 minutes and then in a humid oven at 150° C. for 30 minutes. The cured film passes 10 cycles of cold-crack giving no print at 140° F. (60° C.), has 12–14 in-lb. (0.14–0.16 kg-m) direct impact and has an essentially ripple-free surface.

Referring to Table III, the swelling ratio is an indication of crosslink density. The swelling ratio is a standard test for crosslinking, as is well known in the art and is the ratio of the thickness of a solvent-swollen film to its original thickness prior to contact with solvent.

Likewise, the "cold crack cycles passed" test of column V is also well known in the art and is a test which measures film toughness, adhesion and elongation of a film on metal. A cold crack cycle consists of a 3-minute immersion of the coating in a −51° C. cold bath followed by immediate immersion in a 66° C. hot bath. The cycle is repeated until the coating cracks under the stress of the rapidly expanding and contracting metal. Ten cycles is considered adequate for general purpose coating.

The 140° F. print resistance test measures thermoplasticity and is performed by noting the degree of imprint causes by application of a 2 pound weight to 1 sq. inch of cheesecloth fabric for 30 minutes. The test is carried out in a 140° F. oven. Direct impact is an indication of the film's flexibility and adhesion and is tested by a Gardner Light Duty Variable Impact Tester. This test is likewise well known in the art and may be found to be described in more detail in Gardner Laboratory, Inc., catalog PB 8-2.

The film thickness most useful depends on the particular application of the coated surface. However, film thicknesses of up to 15 mils, or more is satisfactory for most uses.

While the invention have been thus illustrated and described in detail, such description is not exhaustive of the various possible permutations of the invention. Rather, the scope of the invention is to be limited only by a reasonable interpretation of the claims.

We claim:

1. An addition polymer having at least five mers and a molecular weight of up to about 2,000,000 and containing in the backbone of said polymer a plurality of units derived from the group consisting of corresponding acrylic, and methacrylic, acid esters represented by the formula

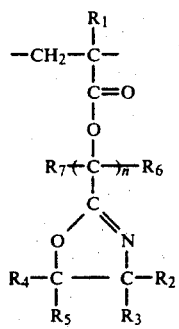

wherein:

n is an integer of from 1 through 20;

$R_1$ is selected from the group consisting of hydrogen and methyl; and $R_2$, $R_3$, $R_4$, $R_5$, $R_6$ and $R_7$ are independently selected from the group consisting of hydrogen and alkyl of from 1 through 20 carbon atoms.

2. A hydrocured thermoset polymer comprising the reaction product of:

(1) a first addition polymer having greater than five mers and a molecular weight of up to about 2,000,000 and containing in the backbone thereof a plurality of units derived from the group consisting of corresponding acrylic, and methacrylic, acid esters represented by the formula

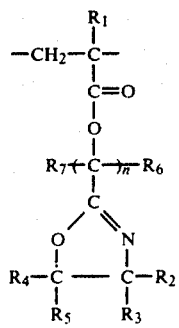

wherein;

n is an integer of from 1 through 20;

$R_1$ is selected from the group consisting of hydrogen and methyl; and $R_2$, $R_3$, $R_4$, $R_5$, $R_6$ and $R_7$ are independently selected from the group consisting of hydrogen and alkyl of from 1 through 20 carbon atoms; with (2) a second addition polymer containing in the backbone thereof a plurality of units derived from addition polymerizable ethylenically unsaturated dicarboxylic acid cyclic anhydrides; and (3) water;

the ratio of said first polymer units to said second polymer units being from about 5:1 to 1:5.

3. The hydrocured thermoset polymer of claim 2 wherein said second addition polymerizable ethylenically unsaturated acid cyclic anhydrides are selected from the group consisting of maleic, itaconic and glutaconic ahydrides.

4. The hydrocured thermoset polymer of claim 3 wherein said first polymer is polymerized from a first monomer mixture comprising from about 20% to 100% by weight of said esters and wherein said second polymer is polymerized from a second monomer mixture comprising from about 2% to 70% by weight of said dicarboxylic acid cyclic anhydrides, the balance of both said first and second monomer mixtures comprising one or more other ethylenically unsaturated monomers.

5. The hydrocured thermoset polymer of claim 4 wherein said other ethylenically unsaturated monomers are selected from the group consisting of esters of $\alpha,\beta$-ethylenically unsaturated monocarboxylic acids, $\alpha,\beta$-ethylenically unsaturated monocarboxylic acids, $\alpha,\beta$-ethylenically unsaturated aldehydes, esters of $\alpha,\beta$-ethylenically unsaturated dicarboxylic acids, $\alpha,\beta$-ethylenically unsaturated dicarboxylic acids, $\alpha,\beta$-ethylenically unsaturated nitriles, hydrocarbons including $\alpha$-olefins and conjugated diolefins, vinylaryl compounds, vinyl alkyl ethers, vinyl halides, vinylidene halides, vinyl sulfides, vinyl acyloxy compounds (esters of saturated carboxylic acids and ethylenically unsaturated alkanols), and vinyl ureido monomers.

6. An article of manufacture comprising the hydrocured thermoset polymer of claim 3.

7. An article of manufacture comprising the hydrocured thermoset polymer of claim 4.

8. An article of manufacture comprising a substrate containing on a surface thereof the hydrocured thermoset polymer of claim 4.

9. An article of manufacture comprising the hydrocured thermoset polymer of claim 4 wherein said first addition poymer has from about 5 to 100 mers.

10. An article of manufacture comprising the hydrocured thermoset polymers of claim 4 wherein said first addition polymer has greater than 100 mers and a molecular weight of up to about 2,000,000.

11. A method of making the hydrocured thermoset polymer of claim 2 comprising the steps of blending (1) a first addition polymer having greater than six mers and a molecular weight of up to about 2,000,000 and containing in the backbone thereof a plurality of units derived from the group consisting of corresponding acrylic, and methacrylic, acid esters represented by the formula

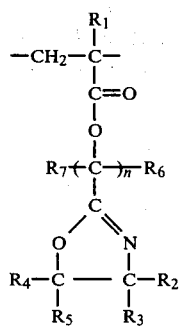

wherein:

n is an integer of from 1 through 20;

$R_2$ is selected from the group consisting of hydrogen and methyl; and $R_2$, $R_3$, $R_4$, $R_5$, $R_6$ and $R_7$ are independently selected from the group consisting of hydrogen and alkyl of from 1 through 20 carbon atoms; with (2) a second addition polymer containing in the backbone thereof a plurality of units derived from addition polymerizable ethylenically unsaturated dicarboxylic acid cyclic anhydrides;

the ratio of said first polymer units to said second polymer units being from about 5:1 to 1:5, heating the blended polymers to a temperature of about 100° C. to about 250° C., thereby fusing the blended polymers and exposing the fused blend to moisture.

12. The method of claim 11 in which said thermoset polymer is obtained as coating of up to about 15 mils in thickness on a solid substrate.

13. The method of claim 12 in which the blended polymers are applied to said substrate as a powder prior to fusing and curring the coating.

14. A hydrocurable polymer blend, capable of yielding a thermoset polymer, comprising:

(1) a first addition polymer having at least five mers and a molecular weight of up to about 2,000,000 and containing in the backbone thereof a plurality of units derived from the group consisting of corresponding acrylic and methacrylic acid esters represented by the formula

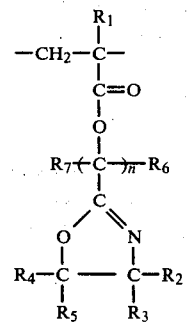

wherein:

n is an integer of from 1 through 20;

$R_1$ is selected from the group consisting of hydrogen and methyl; and $R_2$, $R_3$, $R_4$, $R_5$, $R_6$ and $R_7$ are independently selected from the group consisting of hydrogen and alkyl of from 1 through 20 carbon atoms; with (2) a second addition polymer containing in the backbone thereof a plurality of units derived from addition polymerizable ethylenically usaturated dicarboxylic acid cyclic anhydrides;

the ratio of said first polymer units to said second polymer units being from about 5:1 to 1:5.

* * * * *

UNITED STATES PATENT AND TRADEMARK OFFICE
CERTIFICATE OF CORRECTION

PATENT NO. : 4,247,671
DATED : 27 January 1981
INVENTOR(S) : R. Larry Reitz et al.

It is certified that error appears in the above—identified patent and that said Letters Patent is hereby corrected as shown below:

Column 10, lines 45-50 in EQUATION II, change

" 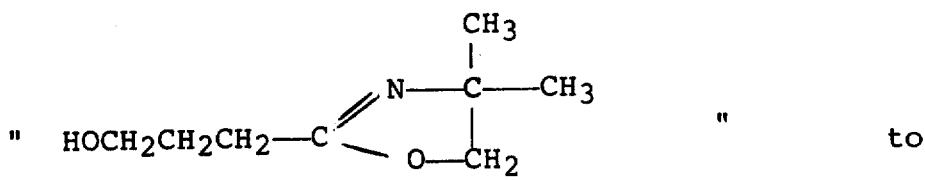 " to

-- 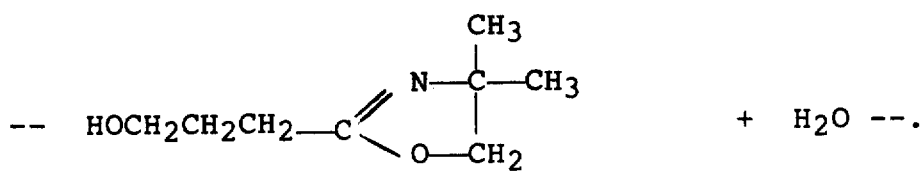 + H₂O --.

Column 13, line 40, change "helf" to --held--.

UNITED STATES PATENT AND TRADEMARK OFFICE
CERTIFICATE OF CORRECTION

PATENT NO. : 4,247,671
DATED : 27 January 1981
INVENTOR(S) : R. Larry Reitz et al.

It is certified that error appears in the above—identified patent and that said Letters Patent is hereby corrected as shown below:

a) Column 15-16, TABLE III, under "Cure Temp." for Anhydride Component 2 and Oxazoline Component D (line 8), change "160" to --150--;

b) under "Direct Impact" for Anhydride Component 3 and Oxazoline Component B (line 1), change "20-26" to --20-25--;

c) also under "Direct Impact" for anhydride Component 2 and Oxazoline Component E (last line), change "0-15" to --10-15--.

Claim 11, column 19, line 17, change "$R_2$" to --$R_1$--.

Signed and Sealed this

Twelfth Day of January 1982

[SEAL]

Attest:

GERALD J. MOSSINGHOFF

Attesting Officer    Commissioner of Patents and Trademarks